US010800594B2

(12) United States Patent
Schwab

(10) Patent No.: US 10,800,594 B2
(45) Date of Patent: Oct. 13, 2020

(54) SECURABLE SAMPLING PORT FOR AN INSULATED CONTAINER

(71) Applicant: Mark Jordan Schwab, Woodbury, MN (US)

(72) Inventor: Mark Jordan Schwab, Woodbury, MN (US)

(73) Assignee: Quality Mangement, Incorporated, Oakdale, MN (US)

( * ) Notice: Subject to any disclaimer, the term of this patent is extended or adjusted under 35 U.S.C. 154(b) by 66 days.

(21) Appl. No.: 15/799,518

(22) Filed: Oct. 31, 2017

(65) Prior Publication Data

US 2019/0127140 A1    May 2, 2019

(51) Int. Cl.
*B65D 85/00* (2006.01)
*G01N 33/04* (2006.01)
(Continued)

(52) U.S. Cl.
CPC .......... *B65D 81/3806* (2013.01); *B60P 3/226* (2013.01); *B65D 43/021* (2013.01);
(Continued)

(58) Field of Classification Search
CPC ......... B65F 3/00; B65D 43/02; B65D 43/165; B65D 90/10; B65D 2251/1058; B65D 2251/20; B65D 43/22; B65D 43/18; B65D 81/3806; B65D 43/021; B65D 41/32; B65D 41/20; B65D 41/50; A01J 9/00; A01J 5/01; A01J 5/045; B60P 3/226; B60P 3/22; A61J 1/1475; B01L 99/00; B01L 3/0296;
(Continued)

(56) References Cited

U.S. PATENT DOCUMENTS 1,429,710 A * 9/1922 Brayshaw ................ G01N 1/10
137/262
3,013,431 A * 12/1961 Splettstoeser .......... G01G 19/00
73/202
(Continued)

FOREIGN PATENT DOCUMENTS

| CA | 2510537 A1 | 12/2005 |
| CN | 206172280 U | 5/2017 |
| WO | 2004022456 A2 | 3/2004 |

OTHER PUBLICATIONS

AK Steel, 316/316L Stainless Steel, Dec. 13, 2016, AK Steel Corporation, https://www.aksteel.com/sites/default/files/2018-01/316316L201706_2.pdf, p. 1 (Year: 2016).*
(Continued)

*Primary Examiner* — Gideon R Weinerth
(74) *Attorney, Agent, or Firm* — Merchant & Gould P.C.

(57) ABSTRACT

Apparatus and installation methods for sampling ports are disclosed. Sampling ports include a port housing and a lid assembly. The lid assembly is configured to sealably close against the port housing. Additionally, the lid assembly can be secured, such as with a lock, to the port housing. In one aspect, the port housing includes a sample mount arrangement configured to receive a sampling assembly. The sample mount arrangement defines a sampling channel and the port housing defines a sampling opening and a first securing mount. The lid assembly includes a latch arrangement and defines a second securing mount.

19 Claims, 19 Drawing Sheets

(51) Int. Cl.
| | |
|---|---|
| *B65D 81/38* | (2006.01) |
| *B65D 43/16* | (2006.01) |
| *B65D 43/22* | (2006.01) |
| *B65D 43/02* | (2006.01) |
| *B65D 43/18* | (2006.01) |
| *B65D 90/10* | (2006.01) |
| *B60P 3/22* | (2006.01) |
| *A01J 9/00* | (2006.01) |
| *A01J 5/04* | (2006.01) |
| *A61J 1/14* | (2006.01) |
| *G01N 1/10* | (2006.01) |

(52) U.S. Cl.
CPC ........... *B65D 43/165* (2013.01); *B65D 43/18* (2013.01); *B65D 43/22* (2013.01); *B65D 90/10* (2013.01); *A01J 5/045* (2013.01); *A01J 9/00* (2013.01); *A61J 1/1406* (2013.01); *B65D 2251/1058* (2013.01); *B65D 2251/20* (2013.01); *G01N 33/04* (2013.01); *G01N 2001/1093* (2013.01)

(58) Field of Classification Search
CPC ............. G01N 1/10; G01N 2001/1031; G01N 2001/1056; G01N 15/0806; G01N 1/2035; G01N 35/1079; G01N 35/1056; G01N 2001/2071; C12Q 1/24; B67D 7/02; G01F 5/00; Y10S 604/905
USPC ..................... 220/592.2, 324, 326, 833, 810; 73/864.91, 863.52; 600/573
See application file for complete search history.

(56) References Cited

U.S. PATENT DOCUMENTS

| | | | | |
|---|---|---|---|---|
| 3,118,561 A * | 1/1964 | Klaus | ................ | F16L 55/1018 220/324 |
| 3,308,669 A * | 3/1967 | Grise | ................ | G01N 1/2035 73/203 |
| 3,528,375 A * | 9/1970 | Trausch | ................ | B61D 5/00 105/358 |
| 3,776,042 A * | 12/1973 | Werra | ................ | G01N 1/14 73/863.85 |
| 3,779,082 A * | 12/1973 | Galloway | ................ | G01N 1/14 73/863.85 |
| 3,930,413 A * | 1/1976 | Laird | ................ | B01L 3/50825 73/863.85 |
| 4,127,215 A * | 11/1978 | Morrison | ................ | B64C 1/1407 220/259.3 |
| 4,174,632 A * | 11/1979 | Jansen | ................ | G01N 1/2035 73/863.86 |
| 4,423,641 A * | 1/1984 | Ottung | ................ | G01N 1/10 137/240 |
| 4,574,630 A * | 3/1986 | Icking | ................ | A01J 5/045 137/625.48 |
| 4,785,676 A * | 11/1988 | DeOca | ................ | G01N 1/10 141/329 |
| 4,805,632 A * | 2/1989 | Pope | ................ | A61B 5/05 340/573.5 |
| 4,927,605 A * | 5/1990 | Dorn | ................ | A61B 10/007 422/557 |
| 4,941,517 A * | 7/1990 | Galloway | ................ | B67B 7/26 141/1 |
| 4,960,346 A | 10/1990 | Tamayo | | |
| 5,086,813 A * | 2/1992 | Galloway | ................ | B67D 7/02 141/1 |
| 5,197,515 A * | 3/1993 | Saville | ................ | B64D 11/02 137/613 |
| 5,199,473 A * | 4/1993 | Galloway | ................ | B67D 7/02 141/312 |
| 5,237,934 A * | 8/1993 | Rhodes | ................ | B65D 90/587 105/282.1 |
| 5,269,350 A * | 12/1993 | Galloway | ................ | B67B 7/26 141/1 |
| 5,660,295 A * | 8/1997 | Hroma | ................ | B65D 90/10 105/377.06 |
| 6,030,580 A * | 2/2000 | Raasch | ................ | B65D 88/745 422/28 |
| D435,906 S * | 1/2001 | Wilkinson | ................ | D24/121 |
| 6,578,647 B2 * | 6/2003 | Page | ................ | E21B 10/25 175/228 |
| 6,715,820 B1 * | 4/2004 | Haas | ................ | B60J 11/06 296/1.04 |
| D494,279 S * | 8/2004 | Cogan | ................ | D24/121 |
| 6,845,676 B2 * | 1/2005 | Bigalke | ................ | G01N 1/2035 73/863.03 |
| 7,272,980 B2 * | 9/2007 | Bigalke | ................ | G01N 1/2035 73/863.85 |
| 8,684,024 B2 | 4/2014 | Kuehn | | |
| 10,399,752 B2 * | 9/2019 | Giraud | ................ | B29C 45/0053 |
| 2002/0185497 A1 | 12/2002 | Joseffy | | |
| 2003/0200822 A1 * | 10/2003 | Layton | ................ | G01N 1/2035 73/864.63 |
| 2007/0125259 A1 * | 6/2007 | Dalrymple | ................ | B61D 5/08 105/236 |
| 2010/0147087 A1 * | 6/2010 | Secord | ................ | G01N 1/2035 73/863.86 |
| 2011/0000919 A1 * | 1/2011 | Whalen | ................ | B65D 25/32 220/500 |
| 2013/0045501 A1 * | 2/2013 | Hu | ................ | B01L 3/502 435/34 |
| 2013/0078735 A1 * | 3/2013 | Sandra | ................ | G01N 30/06 436/175 |
| 2013/0177937 A1 * | 7/2013 | Brown | ................ | B01L 3/508 435/34 |
| 2013/0248531 A1 * | 9/2013 | Lane | ................ | A45C 11/20 220/262 |
| 2015/0216464 A1 * | 8/2015 | Kashmirian | ..... | A61B 5/150343 73/864.91 |
| 2015/0307013 A1 | 10/2015 | Tremblay et al. | | |
| 2016/0345762 A1 * | 12/2016 | Brannock | ................ | A47G 19/2272 |
| 2017/0253168 A1 | 9/2017 | Cannon | | |
| 2018/0222033 A1 * | 8/2018 | Livell | ................ | B25H 3/006 |
| 2019/0120730 A1 * | 4/2019 | Giraud | ................ | G01N 1/14 |

OTHER PUBLICATIONS

Bulk Transporter's Fleet Management, New tremcar farm pick-up trailer keeps drivers and other workers at ground level, Oct. 5, 2015, 4 pages.

\* cited by examiner

SECURABLE SAMPLING PORT FOR AN INSULATED CONTAINER

FIELD OF THE DISCLOSURE

The present disclosure relates to arrangements, features, and installation methods for installing a sampling port, such as secured lidded sampling ports. The methods and apparatus can be applied to insulated containers, including tank trailers configured for milk.

BACKGROUND

Fluids within containers are often sampled throughout a production process. Sampling is performed for a variety of reasons, depending upon the industry and implementation. For instance, fluid samples are drawn to determine quality, to obtain a baseline status for the fluid, to check developments of reactions within the fluid, to determine whether contamination exists, and/or to create a chain of custody as it relates to fluid contents. In some implementations, fluids are held in insulated containers during production and/or transportation, yet sampling of the fluids may still be desirable or required.

SUMMARY

Techniques and apparatus disclosed herein relate to sampling ports for insulated containers. In addition, techniques and apparatus disclosed herein relate to installing sampling ports on previously- and originally-manufactured insulated containers.

In general, sampling ports include a port housing and a lid assembly. The lid assembly is configured to sealably close against the port housing. Additionally, the lid assembly can be secured, such as with a lock, to the port housing. In one aspect, the port housing includes a sample mount arrangement configured to receive a sampling assembly. The sample mount arrangement defines a sampling channel and the port housing defines a sampling opening and a first securing mount. The lid assembly includes a latch arrangement and defines a second securing mount.

Methods and techniques disclosed include installing a secure sampling port on an insulated container. These methods and techniques include generating a mounting volume, which includes creating an outer container passage through an outer container of the insulated container; creating an insulation passage through insulation of the insulated container; and creating an inner container passage through an inner container of the insulated container. Then, the secure sampling port is positioned in the mounting volume. Next, the secure sampling port is connected to the insulated container.

The details of one or more embodiments are set forth in the accompanying drawings and the description below. It is to be understood that both the foregoing summary of the disclosure and the following detailed description are exemplary and intended to provide further explanation without limiting the scope of the disclosure.

BRIEF DESCRIPTION OF THE DRAWINGS

The following figures, which form a part of this application, are illustrative of described technology and are not meant to limit the scope of the claims in any manner.

DETAILED DESCRIPTION

Figure 1:
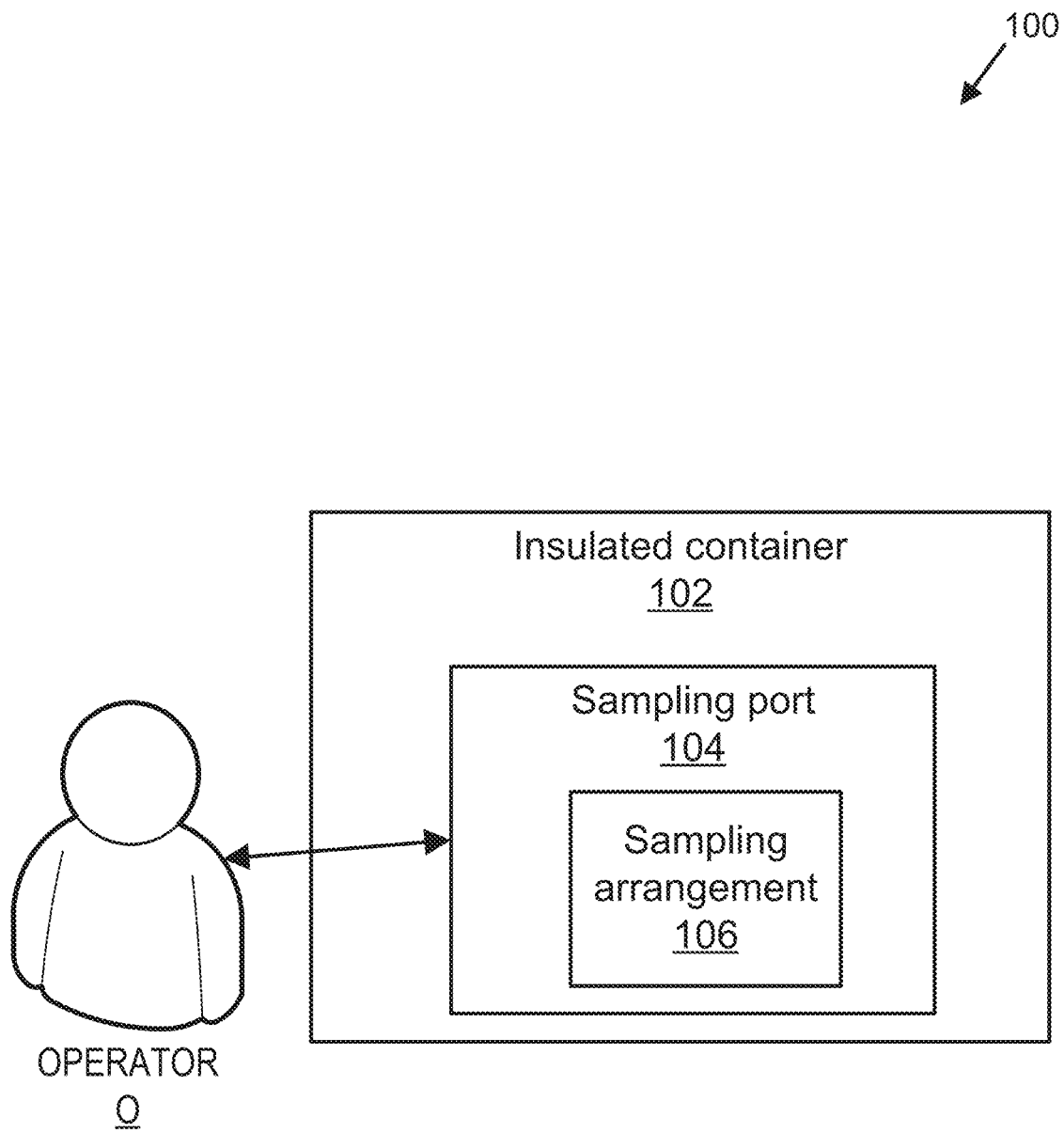
FIG. 1 is a schematic diagram of a fluid sampling environment.

Various embodiments of the present invention will be described in detail with reference to the drawings, wherein like reference numerals represent like parts and assemblies throughout the several views. The features described herein are examples of implementations of certain broad, inventive aspects which underlie the disclosure.

As briefly described above, embodiments of the present disclosure are directed to sampling ports. In particular, embodiments and methods described below relate to an implementation of sampling ports in insulated containers particularly well-suited for transportation of fluids. One example implementation is for an insulated, trailered vehicle configured for hauling milk. That said, aspects underlying this disclosure can be applied to other industries and implementations, such as bulk tanks, silos, and fermentation tanks, to name a few.

Typical milk tanker trailers have two barrels, an inner barrel and an outer barrel, with insulation between the two barrels. Milk samples are obtained throughout milk production processes for a variety of reasons, such as to verify quality and to ensure there is no contamination of the milk product. Conventional sampling scenarios include an operator climbing up a ladder that is mounted on the tanker trailer. Once on top of the trailer, the operator opens up a man-hole and while the man-hole is ajar, scoops out a milk sample. A given operator may be required to perform these operations multiple times for each given milk delivery. While the man-hole cover is open, the milk product is exposed to environmental factors that can be undesirable or deleterious to the milk product. For example, dirt can enter into the milk containing compartment, as well as hair, bird droppings, and the like. Furthermore, climbing up and down the ladder poses inherent safety risks for the operator. Generally, the arrangements, features, and methods contemplated below are directed to avoid the issues mentioned above with existing tanker vehicles and to provide additional functionality for sampling the milk product.

FIG. 1 is a schematic block diagram of an example fluid sampling environment 100. Example fluid sampling environment 100 includes insulated container 102, sampling port 104, and sampling arrangement 106. Also shown is operator O, where operator O interacts with sampling port 104 to obtain one or more samples. Preferably, both sampling port 104 and installation of sampling port 104 on insulated container 102 are approved/certified by 3-A Sanitary Standards, Inc.

Implementations described below relate to retrofitting insulated container 102 with sampling port 104. That is, insulated container 102 was not originally manufactured with sampling port 104. Regardless, principles and concepts disclosed and contemplated herein apply to original products including sampling port 104.

Generally, insulated container 102 holds fluid during one or more stages of production. Insulated container 102 can additionally be heated or refrigerated, although typical milk tanker trailers do not include refrigeration or heating components. Insulated container 102 can be a variety of shapes, but typical configurations of insulated container 102 are generally cylindrical. In most implementations, insulated container 102 is mounted on a wheeled trailer, such that insulated container 102 can be transported. The wheeled trailer is typically a multi-axle trailer configured for connecting to, and being transported by, a tractor, the tractor including a cab portion and engine portion. Additionally, insulated container 102 may have been manufactured with one or more openings, such as a man-hole cover, enabling access to the interior of insulated container 102. Access may be useful or required for sampling, cleaning, and the like.

Sampling port 104 enables operator O to obtain one or more samples of a fluid within insulated container 102. Sampling port 104 also includes components configured to seal sampling arrangement 106 from environmental aspects such as rain, dust, dirt, and the like, during transport of insulated container 102.

Sampling port 104 is typically positioned such that operator O can access sampling arrangement 106 without the use of ladders or otherwise requiring operator O to be off the ground during sampling. Sampling port 104 is secured to insulated container 102.

Sampling port 104 includes a cover and can be securely closed. Securing arrangements used with sampling port 104 can provide identification of the person or entity closing the sampling port 104. Thereby, access can be limited and a chain of custody can be established for who had access to contents of insulated container 102. In some instances, the person driving the trailer including insulated container 102 is not a person (operator O) interacting with sampling port 104. Rather, an operator at a dairy farm closes and seals sampling port 104 and then a different operator at a milk processing facility verifies the identity of the person at sealed sampling port 104 and unseals sampling port 104 at the processing facility.

Sampling arrangement 106 enables aseptic sampling of the fluid within insulated container 102. Operator O can use an instrument, such as a needle, to breach a portion of sampling arrangement 106 and withdraw a fluid sample through sampling port 104. In some instances, sampling arrangement 106 is a limited use unit, wherein it must be replaced after a given number of uses.

Figure 2:
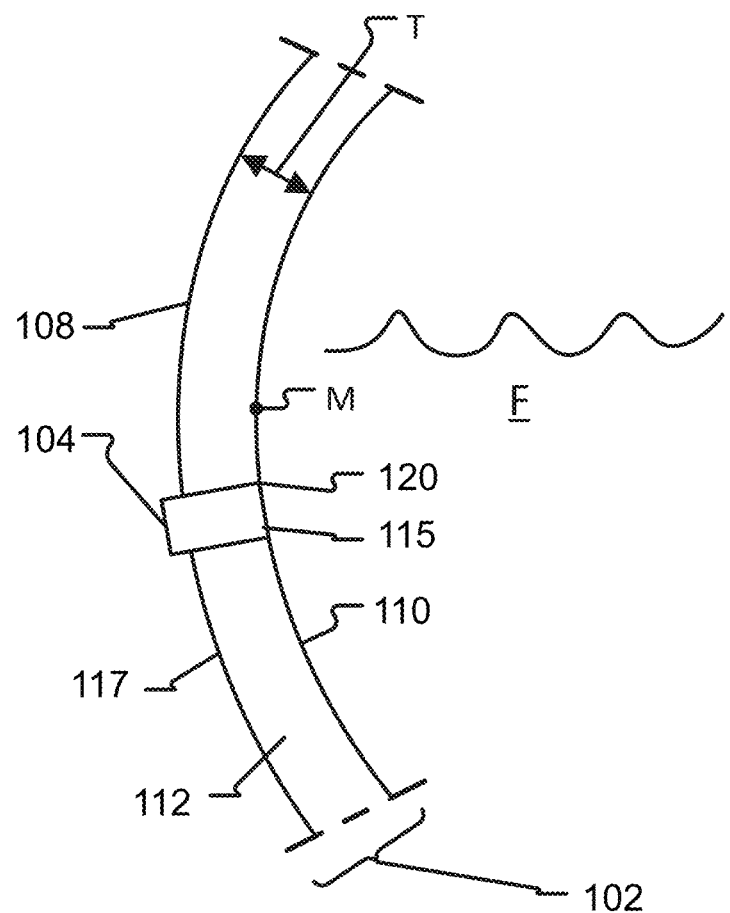
FIG. 2 is a schematic diagram of an insulated container with sampling port of the environment of FIG. 1.

FIG. 2 is a schematic diagram of an insulated container 102 with sampling port 104 positioned thereon. As shown, FIG. 2 is a partial, side-sectional view. Also depicted in FIG. 2 is fluid F which is typically present within insulated container 102 during normal operations. Fluid F is shown schematically within inner container 110 in FIG. 2. Actual fluid levels may vary, such as in different implementations and during different stages of the production process.

Insulated container 102 includes outer container 108, inner container 110, and insulation 112 positioned between outer container 108 and inner container 110. A distance between an outer surface of inner container 110 and an inner surface of outer container 108 is shown as thickness T in FIG. 2. Thickness T generally corresponds to an insulation 112 depth. As shown, both inner container 110 and outer container 108 are generally cylindrical and concentric. Other configurations of inner container 110 and outer container 108 are contemplated.

FIG. 2 shows, schematically, sampling port 104 installed relative to insulated container 102. As shown, sampling port 104 passes through each of outer container 108, insulation 112, and is in contact with inner container 110 at interface 120. Typically, a bottom surface 115 of sampling port 104 is flush and/or coplanar with an inner surface of inner container 110.

Interface 120 is a seam or joint or other interface between sampling port 104 and inner container 110. In typical installation, interface 120 is welded and preferably polished thereby reducing or eliminating ridges, bumps, and other surfaces which can complicate cleaning. Other connection techniques for joining sampling port 104 and inner container 110, in addition to welding, are contemplated. Preferably, both sampling port 104 and installation of sampling port 104 onto insulated container 102 satisfy 3-A SSI certification requirements. In some instances, sampling port 104 is secured to outer container 108.

Also shown schematically in FIG. 2 is that a portion of sampling port 104 extends beyond outer surface 117 of outer container 108. Typically, sampling port 104 includes a flange on an end distal from the end 115 interfacing with inner container 110. Additionally, sampling port 104 includes a lid or cover that is hingably connected and therefore requires room to open. Accordingly, it is preferable to size sampling port 104 relative to thickness T such that an appropriate amount of clearance is provided for the lid on sampling port 104 to open.

Also shown schematically in FIG. 2 is that sampling port 104 is positioned below, and angled slightly downward relative to, a mid-point M of inner container 110. Although the exact location relative to the mid-point M and the ground horizontal can vary by implementation, preferably sampling port 104 is positioned such that an operator of normal height can access and use components within sampling port 104 while still standing on the ground. Additionally, sampling port 104 is preferably oriented such that low fluid F levels can be sampled through sampling port 104. That is, if sampling port 104 is positioned higher than typical fluid levels, such a configuration would render sampling port 104 of little use.

Figure 3:
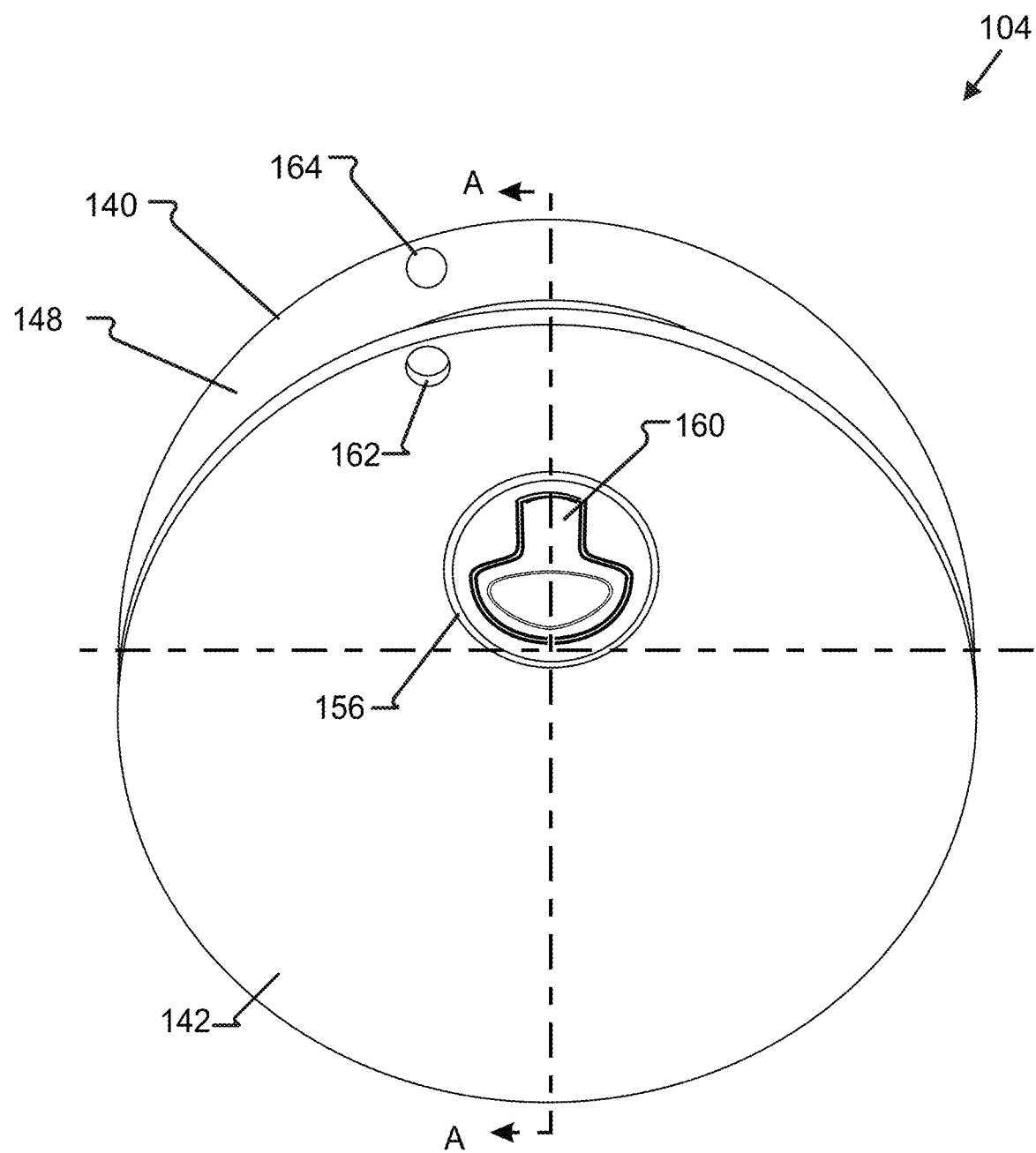
FIG. 3 is a front view of an example embodiment of a sampling port of the environment of FIG. 1.
Figure 4:
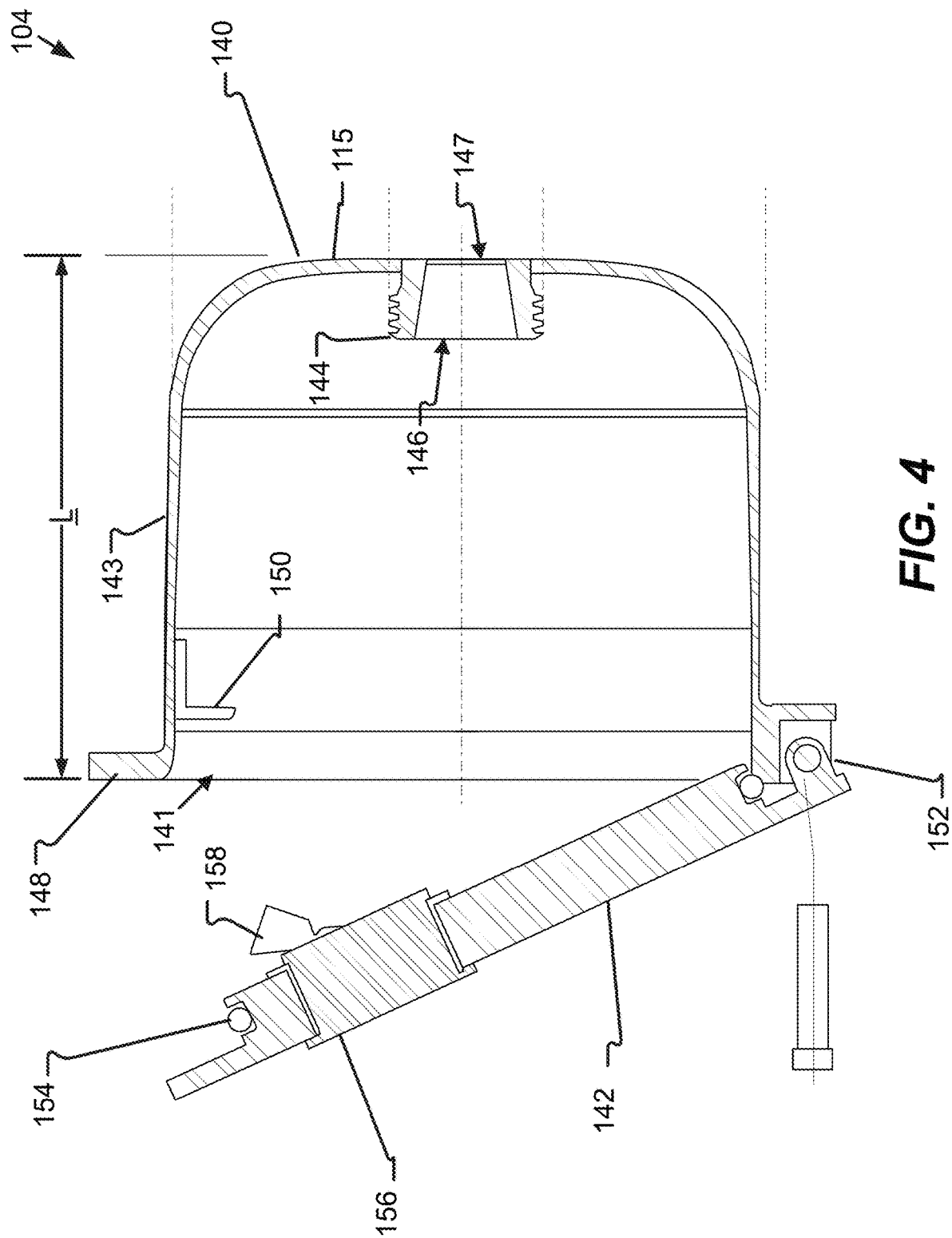
FIG. 4 is a side sectional view along line A-A shown in FIG. 3.
Figure 5:
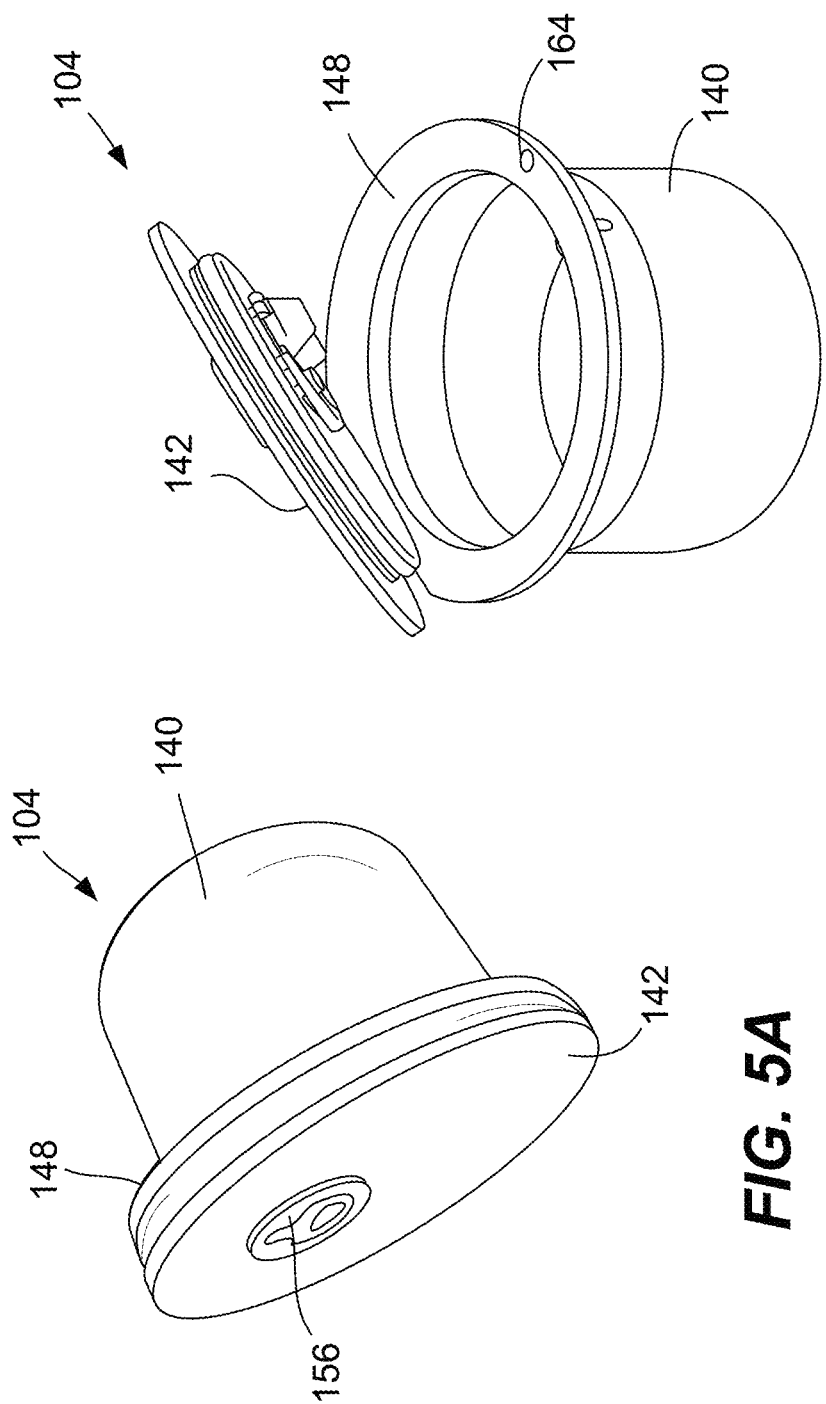
FIG. 5A is a right, top perspective view of sampling port 104.
FIG. 5B is a top, left perspective view of a partially open sampling port 104.
Figure 6:
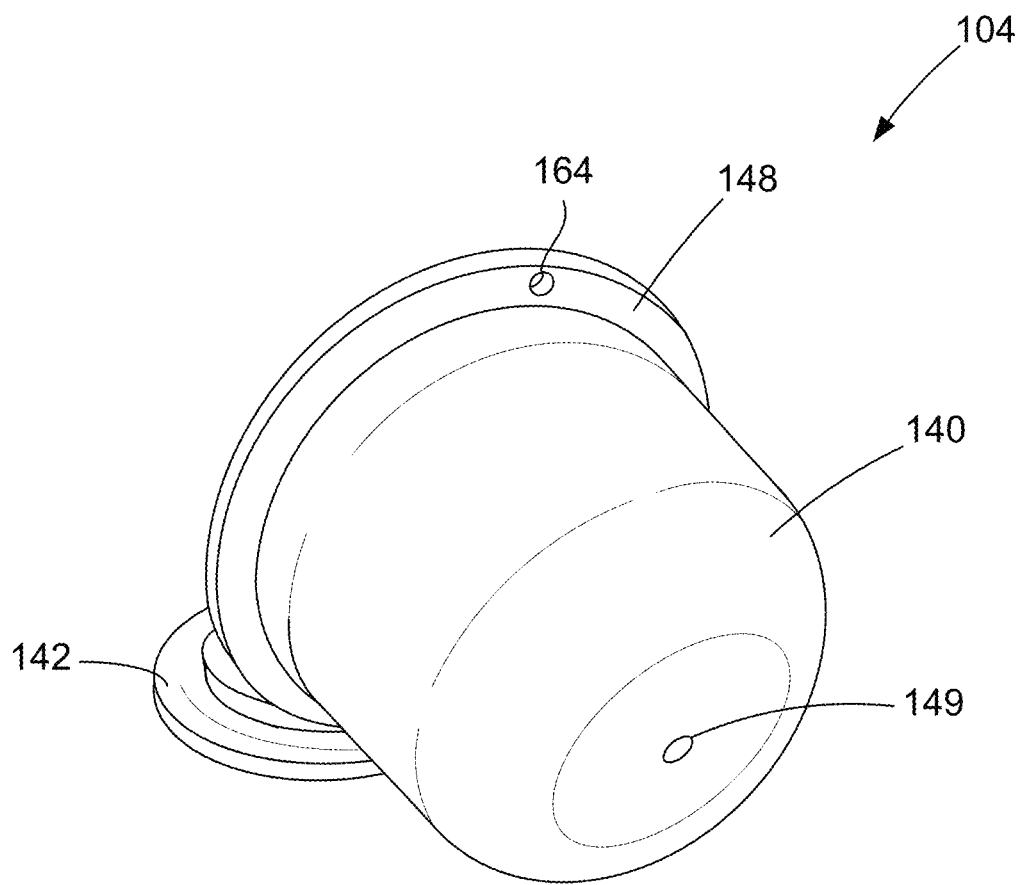
FIG. 6 is a right, rear top perspective view of sampling port 104 as shown in FIG. 5B.
Figure 7:
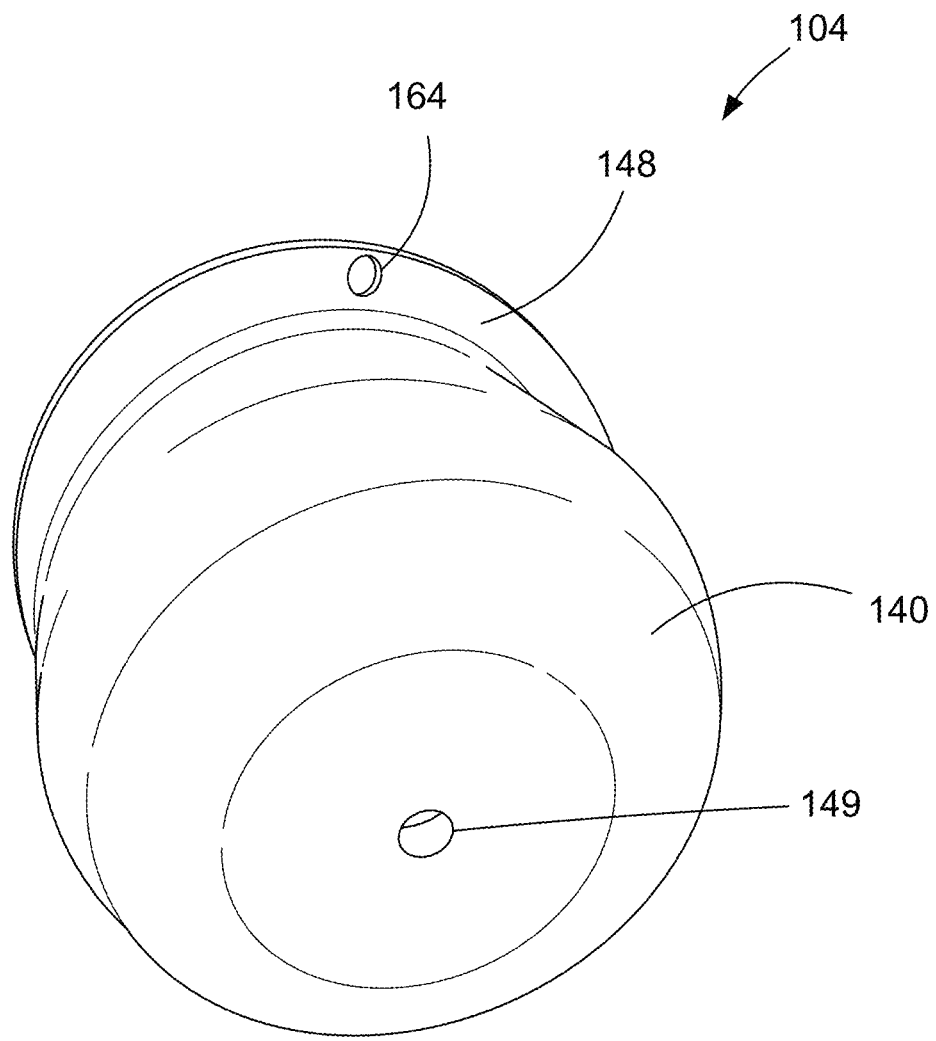
FIG. 7 is a rear top perspective view of sampling port 104 without sampling arrangement 106.
Figure 8:
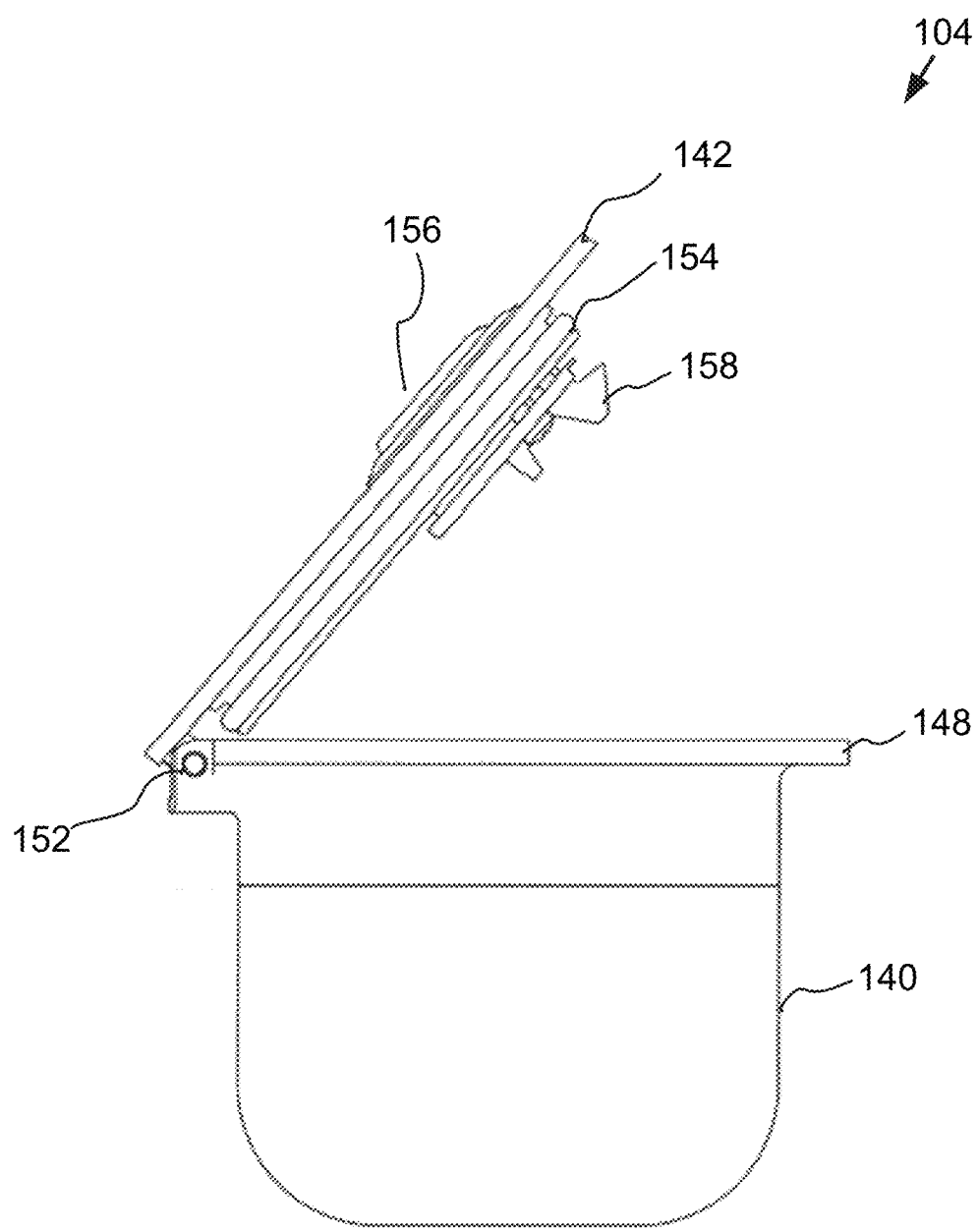
FIG. 8 is a side plan view of sampling port 104.
Figure 9:
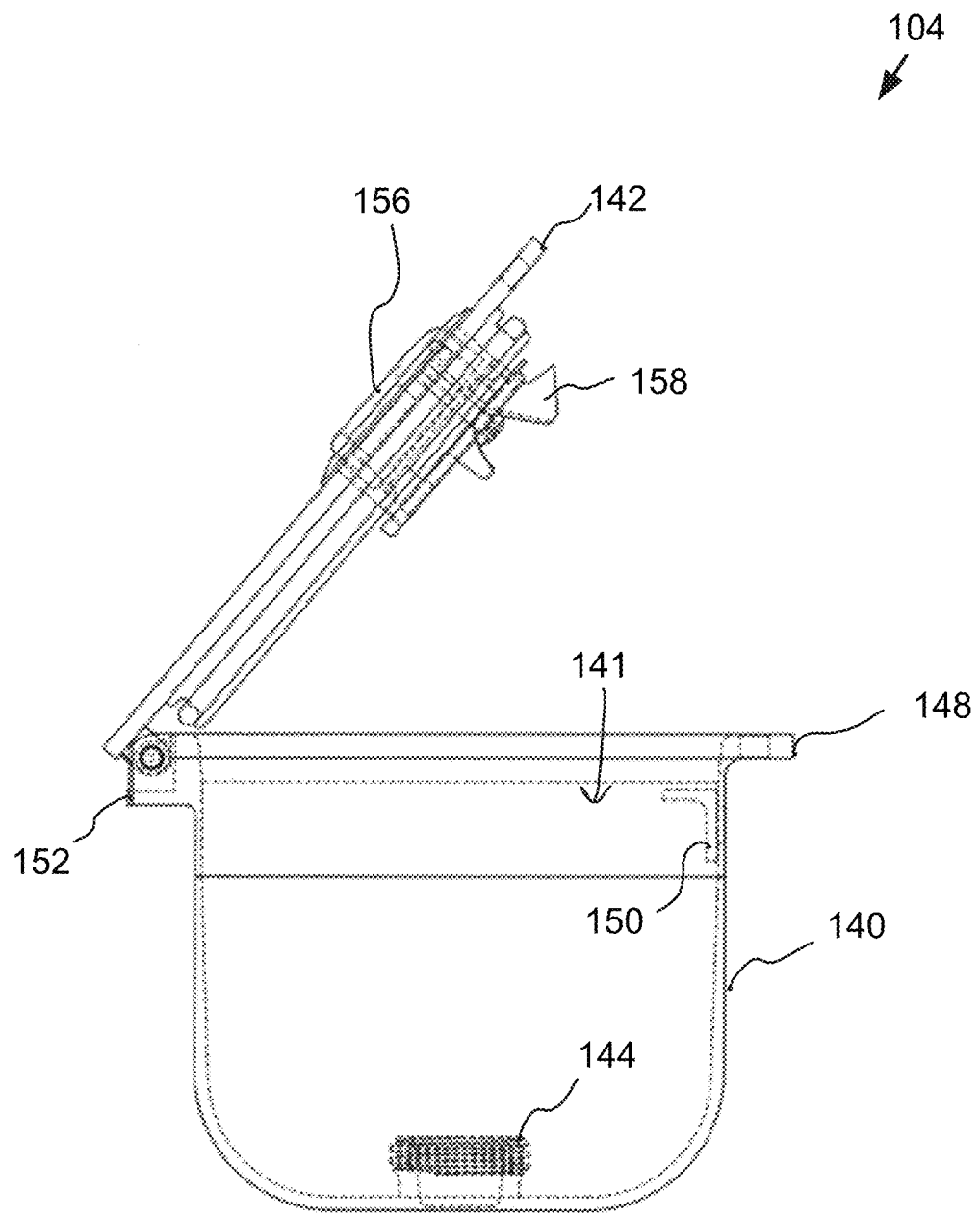
FIG. 9 is a side view of an open sampling port 104 with internal aspects shown in phantom.
Figure 10:
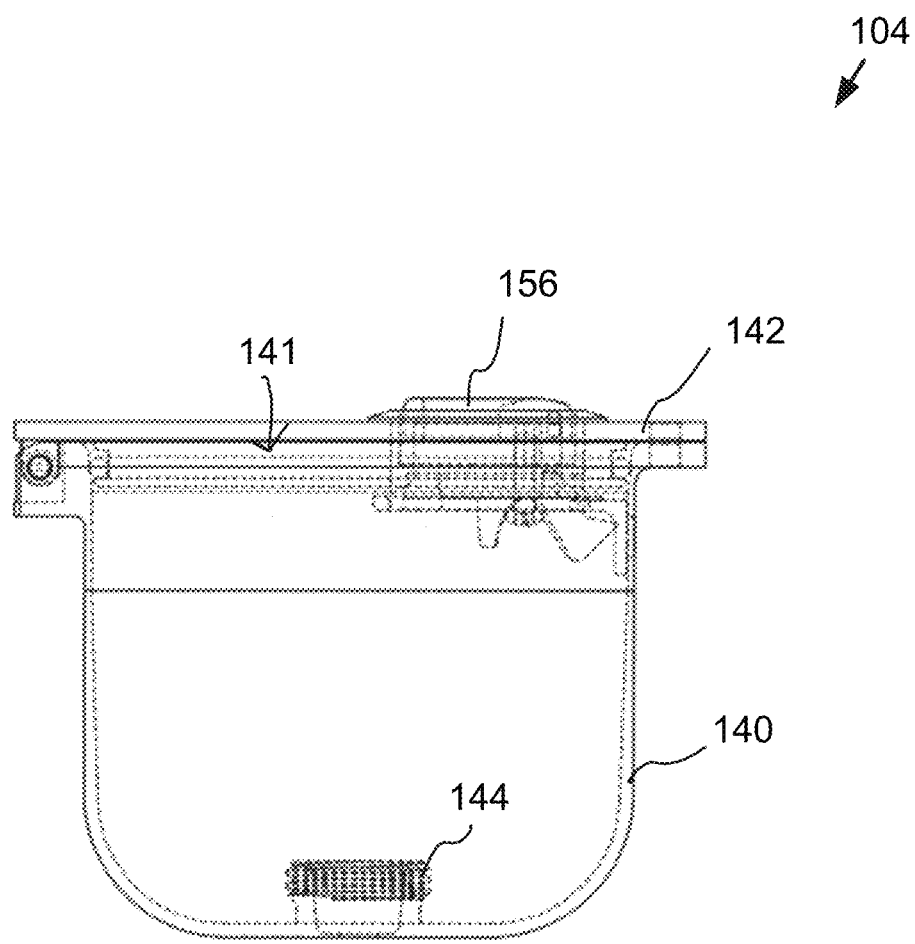
FIG. 10 is a side view of a closed sampling port 104 with internal aspects shown in phantom.
Figure 11:
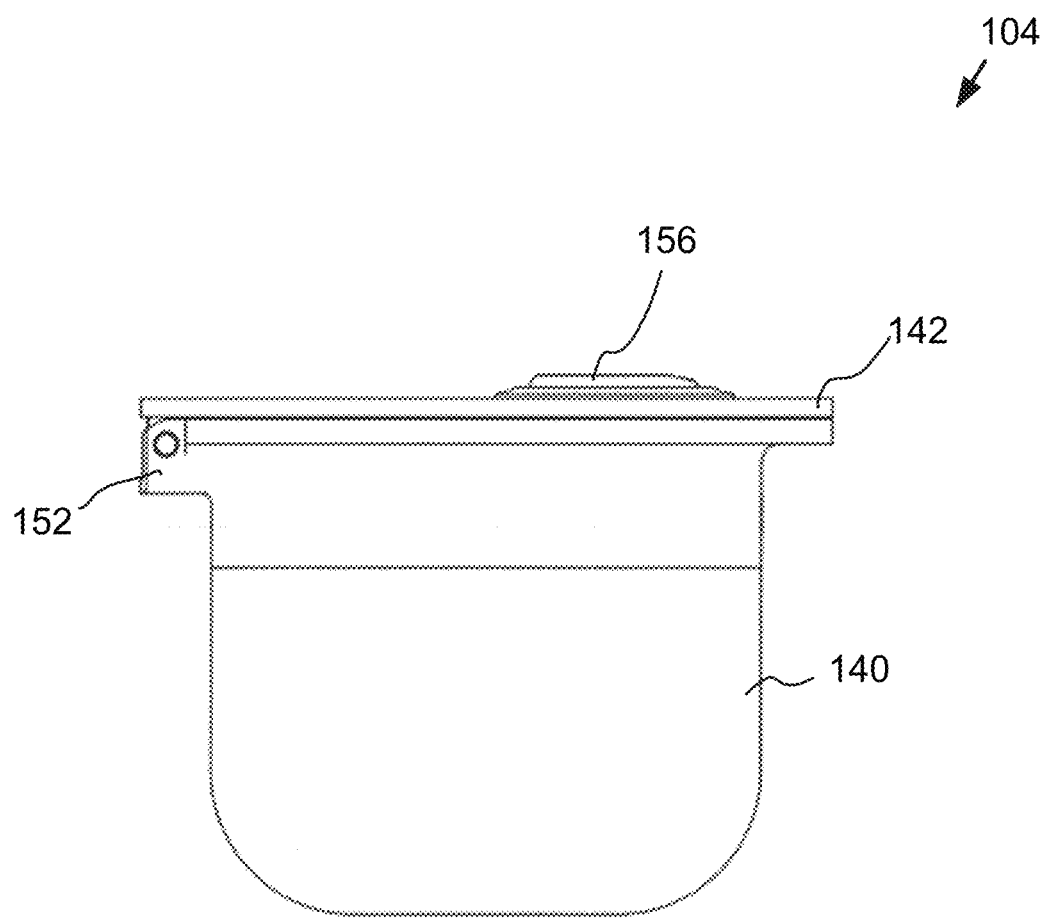
FIG. 11 is a side view of a closed sampling port 104.
Figure 12:
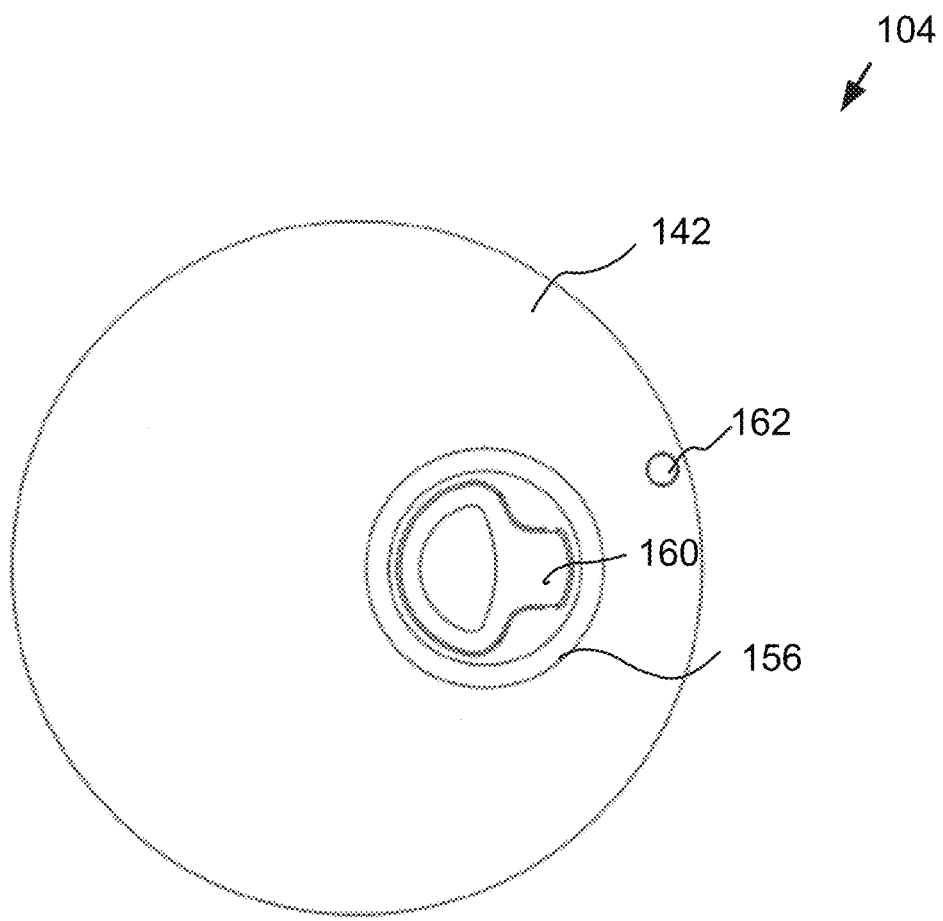
FIG. 12 is a top plan view of sampling port 104.
Figure 13:
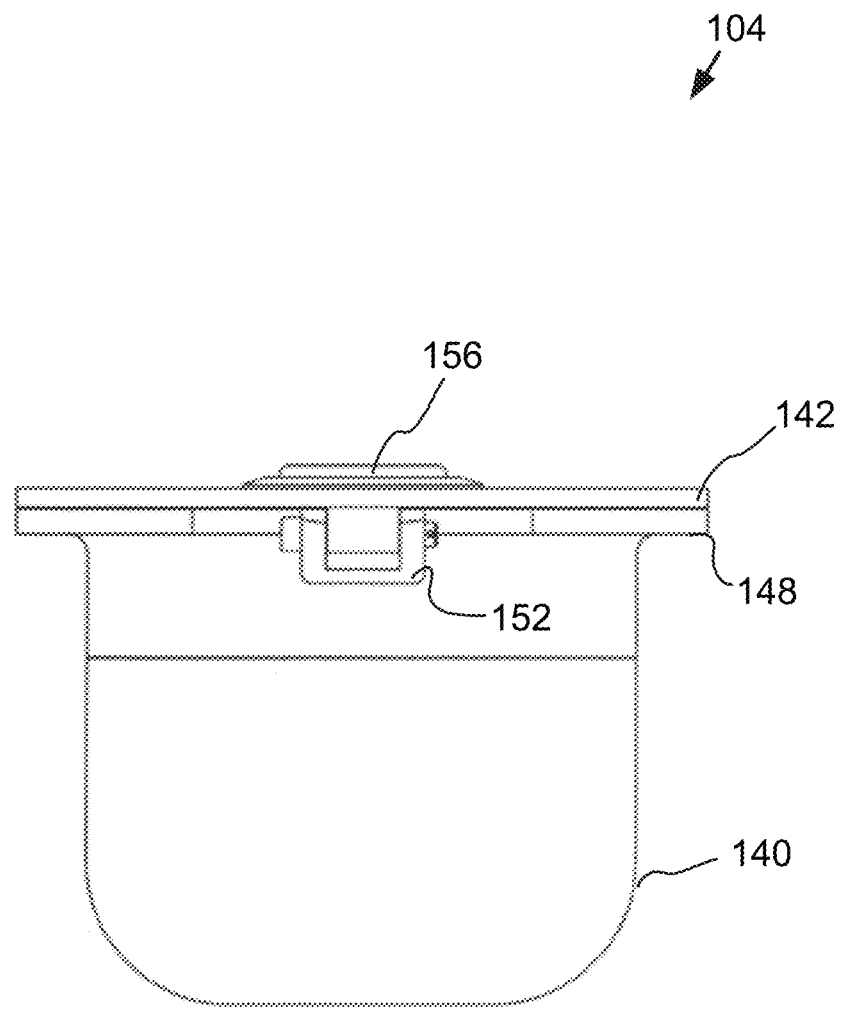
FIG. 13 is a front plan view of sampling port 104.
Figure 14:
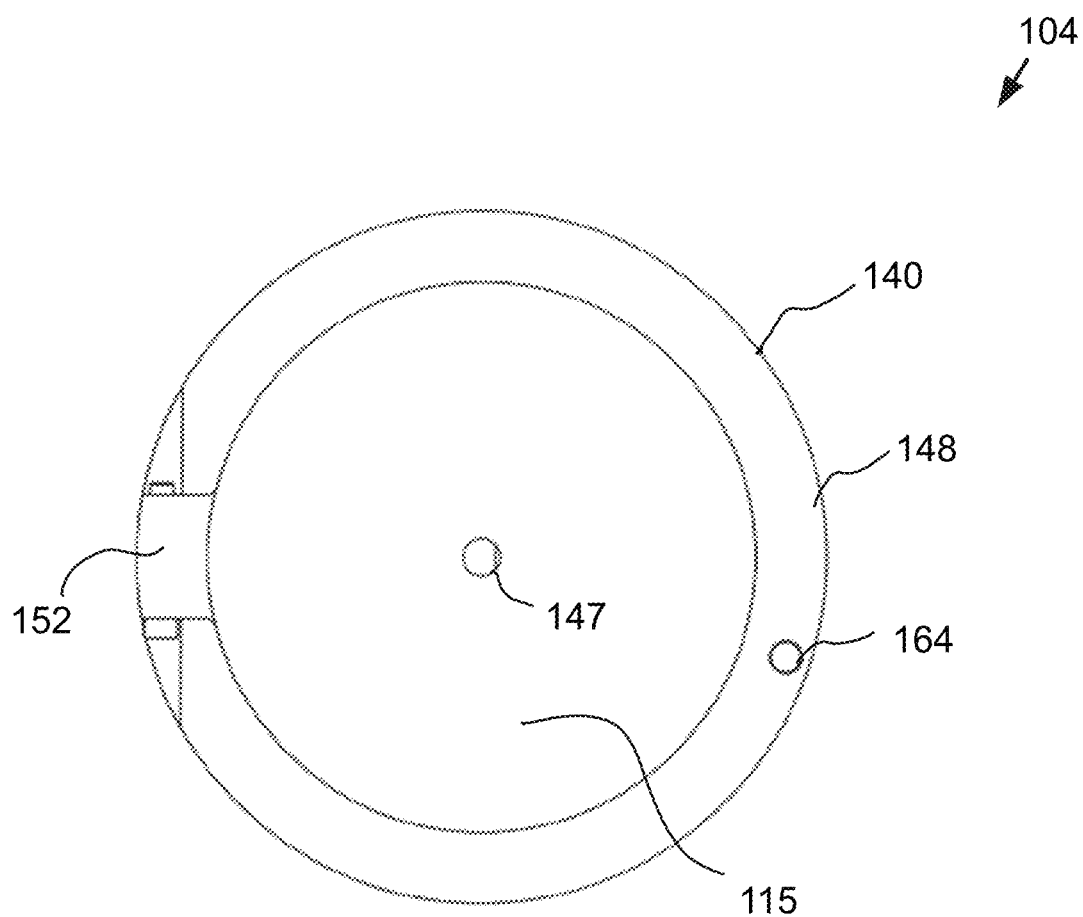
FIG. 14 is a bottom plan view of sampling port 104.
Figure 15:
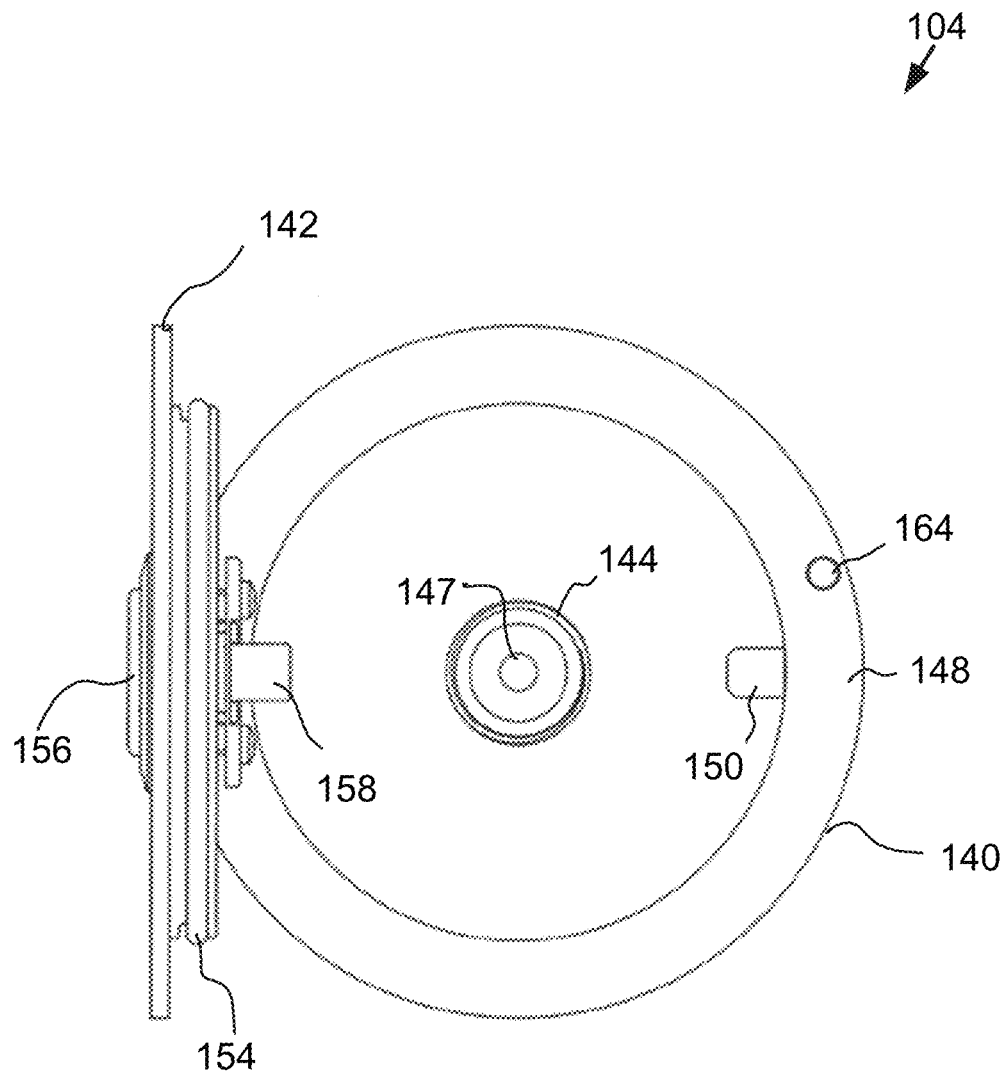
FIG. 15 is a top plan view of an open sampling port 104.

FIGS. 3-15 illustrate an example embodiment of sampling port 104. Broadly, sampling port 104 includes port housing 140 and lid assembly 142. FIG. 3 is a front view of sampling port 104 partially ajar. FIG. 4 is a side sectional view along line A-A shown in FIG. 3. FIG. 5A is a right, top perspective view of sampling port 104. FIG. 5B is a top, left perspective view of a partially open sampling port 104. FIG. 6 is a right, rear top perspective view of sampling port 104 as shown in FIG. 5B. FIG. 7 is a rear top perspective view of sampling port 104 without sampling arrangement 106. FIG. 8 is a side plan view of sampling port 104. FIG. 9 is a side view of an open sampling port 104 with internal aspects shown in phantom. FIG. 10 is a side view of a closed sampling port 104 with internal aspects shown in phantom. FIG. 11 is a side view of a closed sampling port 104. FIG. 12 is a top plan view of sampling port 104. FIG. 13 is a front plan view of sampling port 104. FIG. 14 is a bottom plan view of sampling port 104. FIG. 15 is a top plan view of an open sampling port 104. Unless otherwise noted, FIGS. 3-15 are discussed concurrently below.

Port housing 140 has length L. As noted above, length L is greater than a thickness between the inner container and outer container of insulated container 102. Example length L of port housing 140 includes 5 inches, 5.5 inches, and 6 inches. Other lengths are contemplated and can be adjusted depending upon the implementation and thickness between inner and outer containers.

Port housing 140 defines interior volume 141 enabling access components positioned within port housing 140. Lid assembly 142 selectably encloses interior volume 141. Port housing 140 also defines features enabling lid assembly 142 to securably close. Port housing 140 defines features enabling sampling assembly 106 to mount to port housing 140. As shown, port housing 140 includes cylindrical base portion 143 and flange 148.

Within port housing 140, mount 144 is located in a central position adjacent bottom 115. As shown, mount 144 is threaded thereby enabling a nut or other threaded connector to secure sampling arrangement 106 thereto. In one implementation, mount 144 thread comprises a standard 1.5"-8 ACME thread.

Mount 144 defines sampling passage 146. Sampling passage 146 includes a volume into which a center core member is positioned. Sampling passage 146 is adjacent to sampling opening 149. Sampling opening 149 is a channel through bottom end 115 of port housing 140. Sampling opening 149 is typically smaller in diameter than sampling passage 146. Sampling opening 149 is at least 0.01 inch and usually no greater than 1 inch in diameter. In some instances, sampling opening 149 is no greater than 0.5 inch in diameter. In some instances, sampling opening 149 is no greater than 0.25 inch in diameter. When sampling assembly 106 is installed within port housing 140, interface 147 is formed and is positioned to be in contact with fluid F.

Port housing 140 also includes hinge catch 150. Hinge catch 150 is positioned and configured to provide a surface against which bolt 158 catches when lid assembly 142 is in a closed position. Hinge catch 150 can be a separate component that is welded to port housing 140.

Flange 148 extends radially from port housing 140 and provides mating surfaces for lid assembly 142. Flange 148 also defines port securing mount 164. In the embodiment shown, port securing mount 164 is a channel passing through flange 148. When lid assembly 142 is in a closed position, port securing mount 164 is generally aligned with lid securing mount 162, positioned on lid assembly 142.

Lid assembly 142 is hingably connected to port housing 140 at hinge assembly 152. When sampling port 104 is installed, lid assembly 142 pivots downward toward the ground as it opens. Lid assembly 142 includes seal member 154. Seal member 154 creates a seal between lid assembly 142 and port housing 140 when lid assembly 142 is in a closed position. As shown, seal member 154 is an O ring, typically constructed of rubber compound. Other seal member 154 configurations are contemplated.

Lid assembly 142 includes latch arrangement 156. Latch arrangement 156 enables operator O to open or close lid assembly 142. Additionally, latch arrangement 156 keeps lid assembly 142 in a closed position until it is desired to open lid assembly 142. Latch arrangement includes bolt 158, noted as being configured to mate with hinge catch 150. Latch arrangement 156 also includes latch 160 which, as shown, pivots away from lid assembly 142 and provides a surface for operator O to grab onto when opening lid assembly 142. As shown, latch 160 is spring loaded to keep latch 160 in a substantially flush position during transportation.

Figure 16:
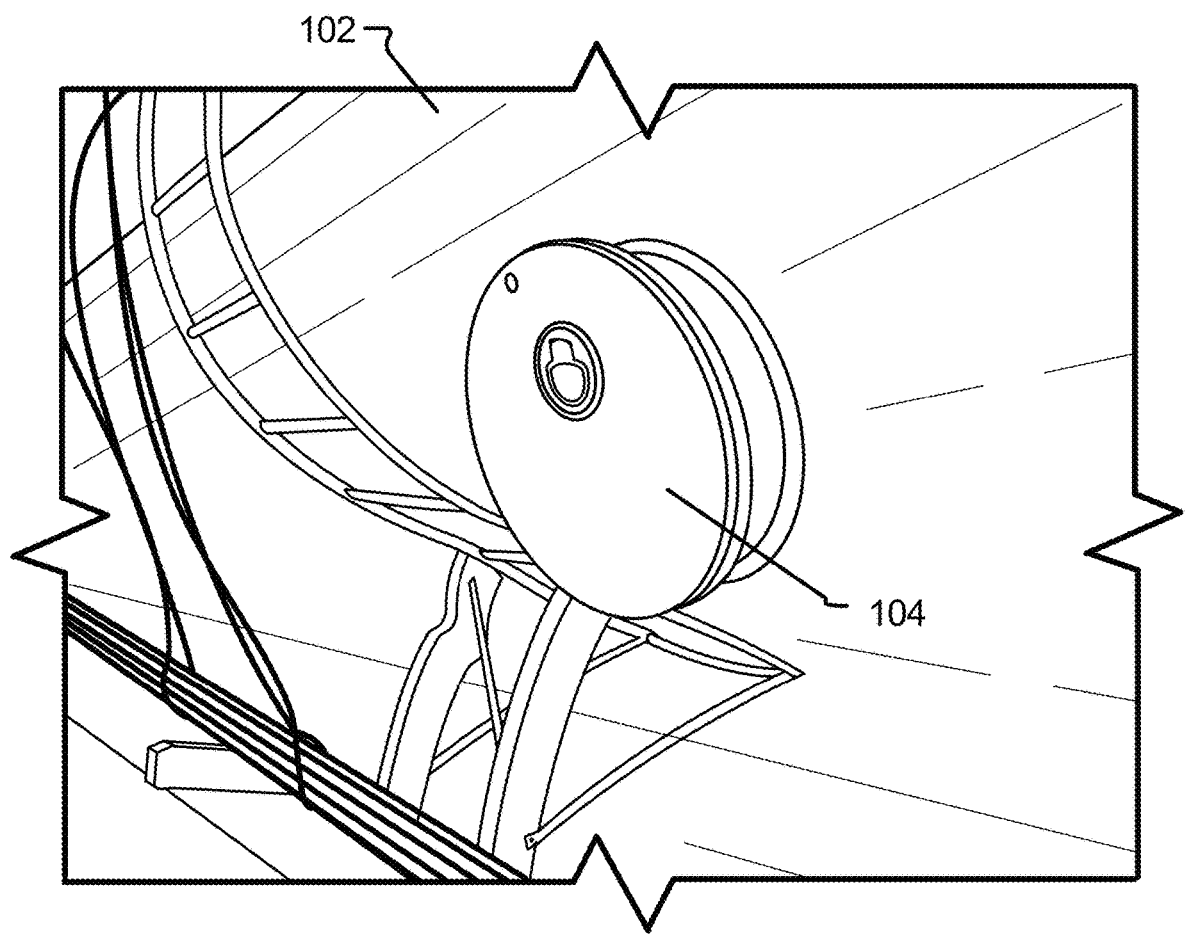
FIG. 16 shows an example embodiment sampling port installed on an insulated container.

FIG. 16 shows example embodiment sampling port 104 installed on insulated container 102. As is evident in FIG. 16, flange 148 is positioned a distance away from an outer surface of outer container 108.

Figure 17:
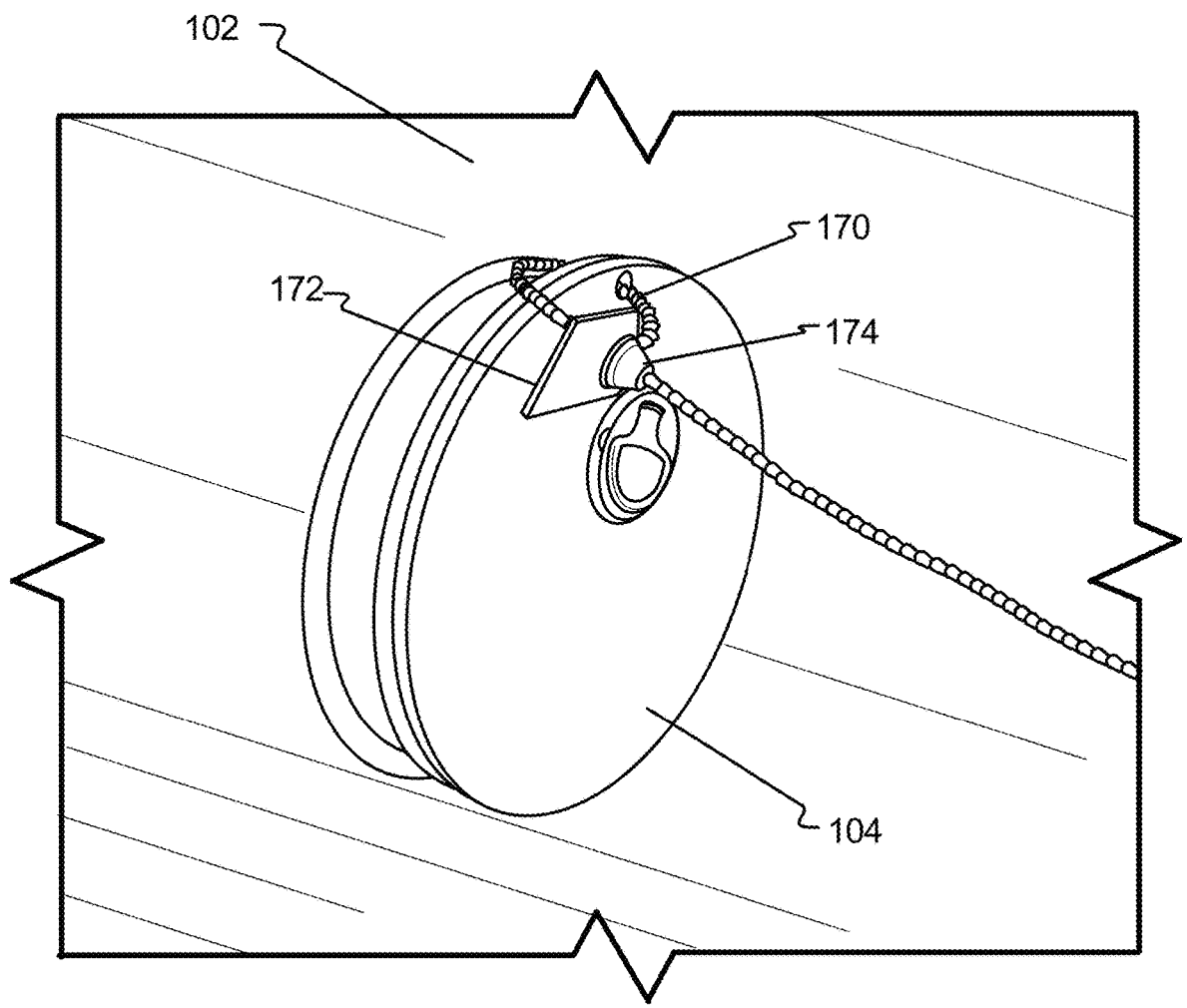
FIG. 17 shows an example embodiment sampling port including a securing arrangement installed on an insulated container.

FIG. 17 shows sampling port 104 installed on insulated container 102. Also shown in FIG. 17 is securing assembly 170. Generally, securing assembly 170 restricts access to the inner volume of sampling port 104 and provides identification of the last person or entity to have access to the sampling assembly 106.

Securing assembly 170 includes identifier tag 172 and locking unit 174. In some instances, identifier tag 172 acts as a transceiver, where identifier tag 172 can receive, store, and provide an identifier. Alternatively, identifier tag 172 can only provide received identifiers, or stored identifiers, upon receiving a communication request. Identifier tag 172 utilizes one or more short range communication protocols. For instance, identifier tag 172 is a radio frequency identification (RFID) tag.

Locking unit 174 engages lid securing mount 162 and port securing mount 164 to effectively lock sampling port 104. In the embodiment shown, locking unit 174 is a form of a zip tie, which is intended to be severed upon arrival of the insulated container 102 at a processing facility. Other locking configurations and techniques are contemplated.

Figure 18:
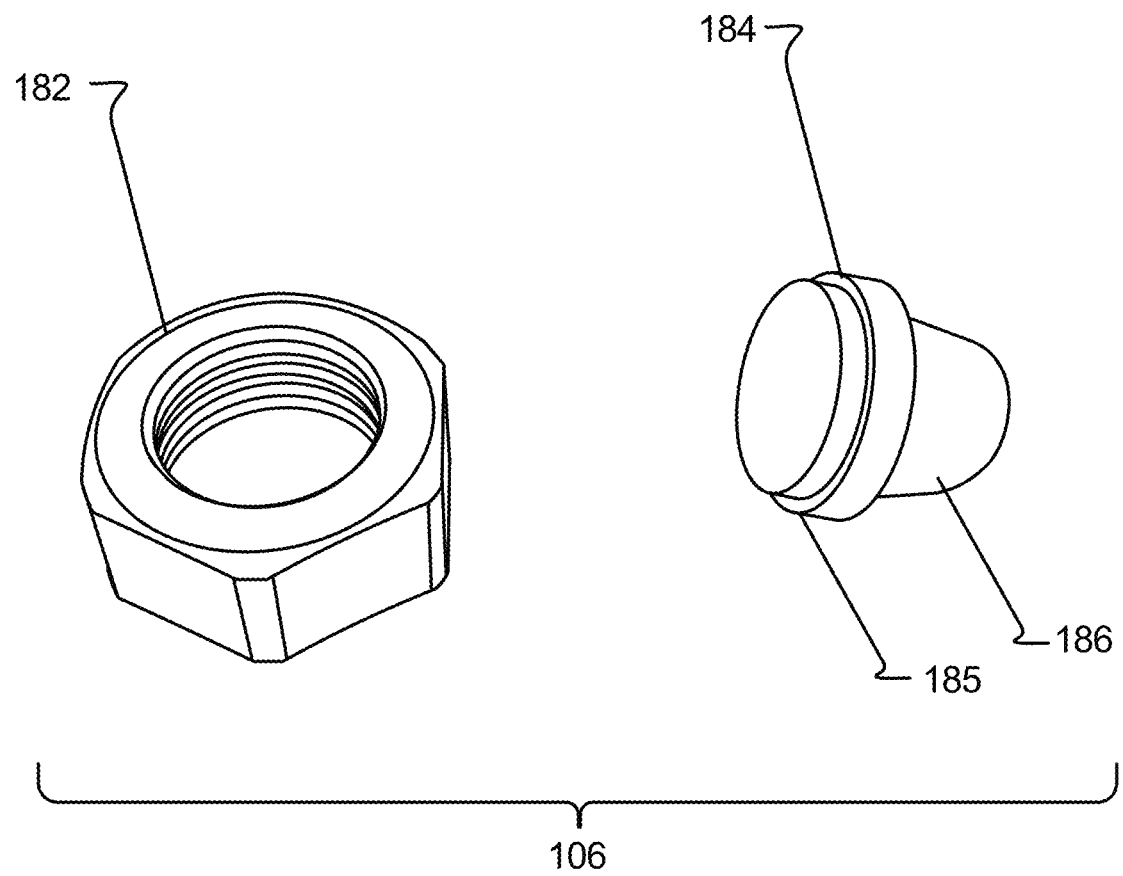
FIG. 18 shows components of an example sampling arrangement.

FIG. 18 shows components of example sampling arrangement 106. Sampling arrangement 106 is configured to couple to mount arrangement 144 and provide capability for aseptic fluid sampling. Sampling arrangement 106 includes securing member 182 and septum unit 184. Example arrangements and configurations of sampling arrangement 106, including septum unit 184, are shown and described in U.S. Pat. No. 6,845,676, "Continuous Fluid Sampler and Method," the entirety of which is hereby incorporated by reference.

Securing member 182 secures septum unit 184 to mount arrangement 144. Preferably, securing member 182 forms a removable coupling to mount arrangement 144 such that septum unit 184 can be removed and replaced upon the end of its useful life. As shown, securing member 182 is a threaded nut. However, securing member 182 can be alternatively configured to mate with different configurations of mount arrangement 144. Other types of fasteners commonly used as securing or retaining means within this context are contemplated and may include, for example, a hex nut, a knurled lock nut, or a keyed nut.

Septum unit 184 provides a plurality of aseptic sampling locations. An example commercial embodiment of septum unit 184 is the QualiTru 7-Port Aseptic Septum (QualiTru Sampling Systems, Oakdale, Minn.).

Septum unit 184 includes cap 185 and center core member 186. In some implementations, when installed, there is compressive contact between mount arrangement 144 and center core member 186. A bottom portion of center core member 186 is flush with, or extends slightly beyond, bottom 115 of the port housing. Center core member 186 thereby forms a seal. The bottom portion of center core member 184 is in communication with fluid within the interior container.

Septum unit 184 generally comprises a plurality of guide holes formed through cap 185. Center core member 186 may be made of material that is generally considered to be of a rubber compound. While compounding of an acceptable rubber composition is believed to be within the skill of the rubber molding art, it is found that rubber compounds based on ethylene propylene diene monomer terpolymer (EPDM) are particularly advantageous, having suitable sealing characteristics. EPDM is a known elastomer, and recognized by those skilled in the polymer arts. Other elastomers are contemplated, such as those derived from, or modified with, butene isoprene, ethylene, and the like. In an alternative embodiment, center core member 186 may comprise a silicon compound. Silicon also provides suitable sealing characteristics. Materials such as Viton or other FDA approved elastomers are also contemplated for use in manufacture of center core member 186.

Figure 19:
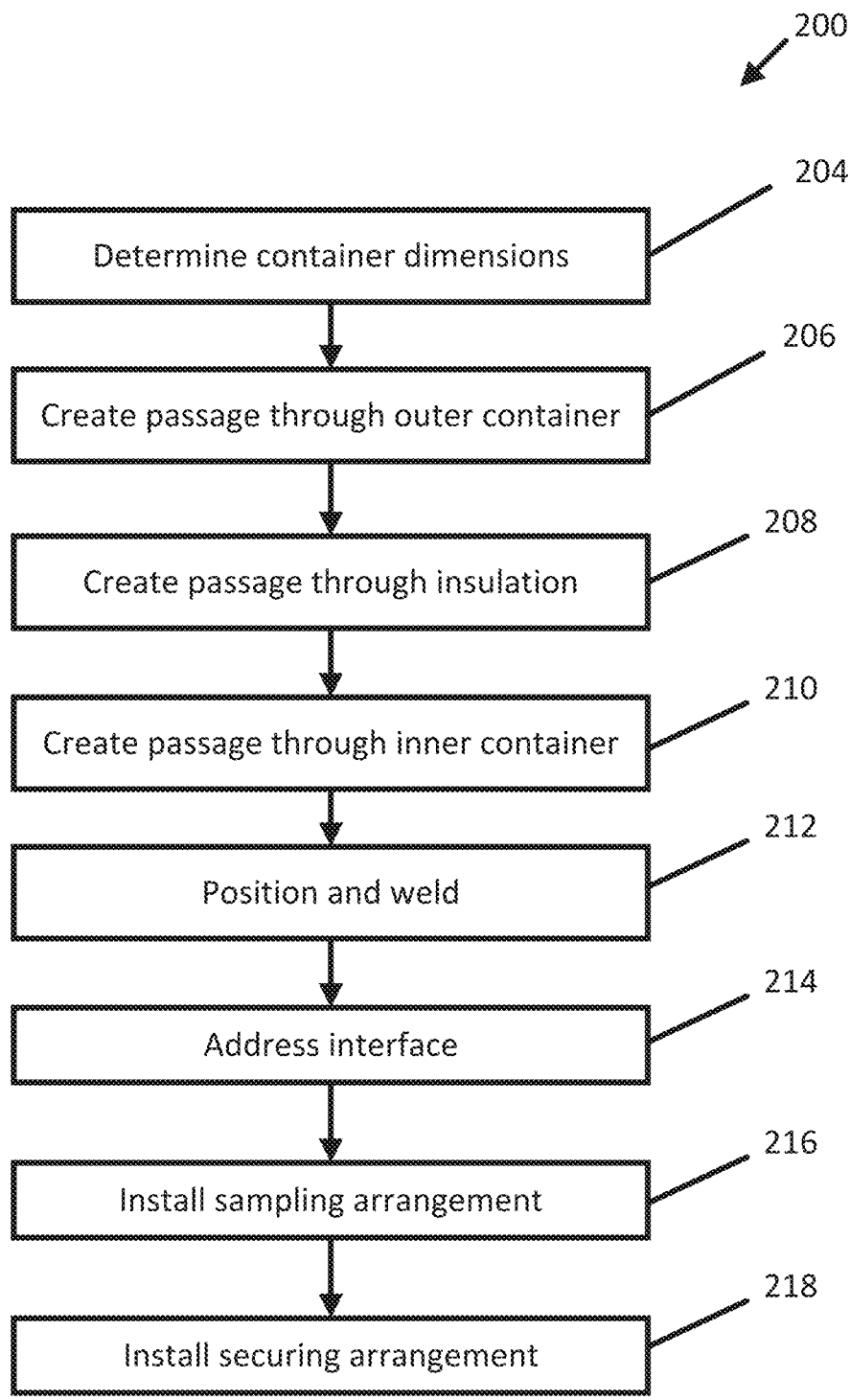
FIG. 19 shows an example method for installing a sampling port on an insulated container.

FIG. 19 shows an example method 200 for installing a sampling port on an insulated container. Example method 200 includes determining container dimensions (operation 204), creating a passage through outer container (operation 206), creating a passage through insulation (operation 208), creating a passage through an inner container (operation 210), positioning and welding (operation 212), addressing interface (operation 214), installing sampling arrangement (operation 216), and installing securing arrangement (operation 218). Example method 200 is typically performed interacting with example components of environment 100 described above. Other embodiments can include more or fewer operations.

Example method 200 begins by determining container dimensions (operation 204). As mentioned above, sampling port 104 is particularly well suited for retrofitting a previously manufactured insulated container 102. Accordingly, owing to variances between different types of insulated containers, a distance between inner and outer containers is determined prior to defining or designing the length of sampling port 104. Generally speaking, there is no industry standard for the amount of insulation between an inner and outer container, such that dimensions of insulated containers are equivalent regardless of manufacturer. For instance, a particular manufacturer may produce a milk tanker trailer having an insulation depth of 4.5 inches. A different manufacturer may produce a milk tanker trailer with an insulation depth of 3.5 inches. It is possible, therefore, that sampling ports of different lengths may be manufactured and installed in accordance with thickness of the insulation layers and/or a distance between the inner and outer containers. In some instances, example method 200 begins at operation 206 because the container dimensions are known.

Next, a passage is created through the outer container (operation 206). Typically, the passage has a diameter equal to, or slightly greater than, an outer diameter of the sample port housing diameter. The shape of the passage corresponds to the shape of the sampling port. For example, a sampling port having a cylindrical housing would dictate a circular cross-section passage through the outer container.

Creating a passage through the outer container (operation 206) generally generating a hole in the outer container. In some implementations, a hole saw drill bit is used to puncture a circular hole in the outer container. The diameter of the hole saw varies depending upon the corresponding size of the sampling port, but in one example implementation the hole saw drill bit used during operation 206 is 5 inches.

Then a passage is created through insulation (operation 208). During operation 208, insulation is removed such that a volume is created enabling the installation of the sampling port.

After removing insulation and creating a passage therethrough (operation 208) a passage is created through an inner container (operation 210). The diameter of the passage through the inner container is less than the diameter of the port housing at the bottom end. Creating a passage through the inner container (operation 210) typically includes generating a hole in the inner container. In some implementations, a hole saw drill bit is used to puncture a circular hole in the inner container. The diameter of the hole saw varies depending upon the corresponding size of the sampling port, but in one example implementation the hole saw drill bit used during operation 210 is 2.5 inches.

Then the port housing is positioned and welded (operation 212) such that the bottom surface of the sampling port is co-planar or flush with the inner container. In some instances, welding may be applied at the interface between the port housing and outer container. Positioning and welding (operation 212) can include applying caulk material at the interface of the sample port housing and the outer container. In some implementations, such as tank trailers, caulking the interface at the outer container enables the sample port to move independent, or somewhat independently of, outer container, where the outer container is configured to flex and/or move during transportation.

After welding (operation 212), the interface between the bottom of the sampling port and the inner container is addressed (operation 214). Operation 214 can include polishing or sanding of the weld. Operation 214 includes removing surface artifacts that could potentially gather or hold particles that may compromise the quality or integrity of the fluid within the inner container. Preferably, the interface is modified so that it conforms with 3-A standards.

Next, a sampling arrangement is installed in the sampling port (operation 216). The sampling arrangement includes a septum unit that is positioned on the mount arrangement. Septum unit includes a securing member and a center core member. Operation 216 includes positioning the center core member and then securing center core member to the mount arrangement with a securing member.

At some point after installation and cleaning, a securing arrangement is installed (operation 218). Installing the securing arrangement (operation 218) can include providing an identifier to an identifier tag, where the identifier corresponds to an entity or an operator. Installing the securing arrangement (operation 218) additionally includes locking the lid to the housing with the securing arrangement.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope contemplated by the present disclosure. Numerous other changes may be made which will readily suggest themselves to those skilled in the art and which are encompassed in the spirit of the disclosure.

What is claimed is:

1. A sampling port, comprising:
   a port housing having a base portion and a bottom portion defining an interior volume;
   a sample mount arrangement extending from the bottom portion and surrounded by the base portion such that the sample mount arrangement is contained inside the interior volume, the sample mount arrangement configured to mount a sampling assembly inside a sampling passage connecting the interior volume to a sampling opening on the bottom portion; and
   a lid assembly configured to sealably mate with the base portion of the port housing to securably enclose the sampling assembly inside the interior volume, the lid assembly including a latch arrangement.

2. The sampling port according to claim 1, further comprising a securing assembly, the securing assembly including a locking arrangement and an identifier tag.

3. The sampling port according to claim 2, wherein the locking arrangement engages a first securing mount on the port housing and a second securing mount on the lid to provide a secured configuration for the sampling port.

4. The sampling port according to claim 3, further comprising a flange that extends radially from the base portion of the port housing, the flange providing a mating surface for the lid assembly and including the first securing mount.

5. The sampling port according to claim 1, further comprising a hinge assembly, the hinge assembly operably connecting the lid assembly to the port housing.

6. The sampling port according to claim 1, the sampling opening being at least 0.015 inches in diameter and no greater than 1 inch in diameter.

7. The sampling port according to claim 6, the sampling opening being no greater than 0.5 inches in diameter.

8. The sampling port according to claim 7, the sampling opening being no greater than 0.25 inches in diameter.

9. The sampling port according to claim 1, further comprising the sampling assembly coupled to the sample mount arrangement, the sampling assembly including a septum unit,
   the septum unit including a securing member and a center core member, the center core member including a plurality of guide holes.

10. The sampling port according to claim 9, the securing member and the sample mount arrangement being threaded;
    the center core member extending to the sampling opening and forming a sealed connection thereto; and
    the center core member being made of a rubber compound material.

11. The sampling port according to claim 10, the sampling port having a port housing length; and
    wherein the sampling port is structured to be positioned on an insulated container such that at least a portion of the port housing length extends through an insulated portion of the insulated container.

12. The sampling port according to claim 1, at least a portion of the port housing being 316L stainless steel.

13. The sampling port according to claim 1, wherein the latch arrangement is structured to latch onto a hinge catch that extends from an interior surface of the base portion to securably enclose the sampling assembly inside the interior volume.

14. A secure sampling port, comprising:
    a port housing having a base portion and a bottom portion defining an interior volume;
    a sample mount arrangement extending from the bottom portion and surrounded by the base portion such that the sample mount arrangement is contained inside the interior volume;
    a flange extending radially from the base portion of the port housing, the flange providing a mating surface that includes a first securing mount;
    a lid assembly configured to sealably mate with the mating surface of the flange, the lid assembly including a latch arrangement, and the lid assembly defining a second securing mount that is alignable with the first securing mount;
    a securing assembly, the securing assembly including a locking arrangement and an identifier tag, the locking arrangement engaging the first securing mount and the second securing mount when the sampling port is in a secured configuration; and
    a sampling assembly coupled to the sample mount arrangement, the sampling assembly including a septum unit, the septum unit including a securing member and a center core member, the center core member including a plurality of guide holes.

15. The secure sampling port according to claim 14, wherein the latch arrangement is structured to latch onto a hinge catch that extends from an interior surface of the base portion to securably enclose the sampling assembly inside the interior volume.

16. The secure sampling port according to claim 14, wherein securing member of the septum unit includes threads that engage corresponding threads on the sample mount arrangement to couple the sampling assembly to the sample mount arrangement.

17. The secure sampling port according to claim 16, wherein the threads on the sample mount arrangement are external threads.

18. The secure sampling port according to claim 14, wherein the sample mount arrangement is configured to mount the sampling assembly inside a sampling passage connecting the interior volume to a sampling opening on the bottom portion.

19. The secure sampling port according to claim 18, wherein the sampling opening is smaller in diameter than the sampling passage.

* * * * *